United States Patent
Sanderberg et al.

(10) Patent No.: US 10,093,618 B2
(45) Date of Patent: Oct. 9, 2018

(54) PROCESS FOR THE PREPARATION OF A POLYUNSATURATED KETONE COMPOUND

(71) Applicant: Avexxin AS, Trondheim (NO)

(72) Inventors: Marcel Sanderberg, Oslo (NO); Inger-Reidun Aukrust, Oslo (NO)

(73) Assignee: Avexxin AS, Trondheim (NO)

( * ) Notice: Subject to any disclaimer, the term of this patent is extended or adjusted under 35 U.S.C. 154(b) by 43 days.

(21) Appl. No.: 14/907,147

(22) PCT Filed: Jul. 23, 2014

(86) PCT No.: PCT/EP2014/065853
§ 371 (c)(1),
(2) Date: Jan. 22, 2016

(87) PCT Pub. No.: WO2015/011206
PCT Pub. Date: Jan. 29, 2015

(65) Prior Publication Data
US 2016/0159737 A1    Jun. 9, 2016

(30) Foreign Application Priority Data
Jul. 24, 2013 (GB) .................................. 1313238.6

(51) Int. Cl.
| C07C 319/14 | (2006.01) |
| C07C 319/26 | (2006.01) |
| C07C 319/02 | (2006.01) |
| C07C 327/22 | (2006.01) |

(52) U.S. Cl.
CPC .......... *C07C 319/14* (2013.01); *C07C 319/02* (2013.01); *C07C 319/26* (2013.01); *C07C 327/22* (2013.01)

(58) Field of Classification Search
CPC ... C07C 319/02; C07C 319/14; C07C 319/26; C07C 327/22
See application file for complete search history.

(56) References Cited

U.S. PATENT DOCUMENTS

| 7,687,543 | B2 | 3/2010 | Johansen et al. |
| 8,524,776 | B2 | 9/2013 | Johansen et al. |
| 8,796,251 | B2 | 8/2014 | Johansen et al. |
| 8,865,768 | B2 | 10/2014 | Johansen et al. |
| 9,187,396 | B2 | 11/2015 | Johansen et al. |
| 2013/0245127 | A1 | 9/2013 | Feuerherm et al. |
| 2015/0202165 | A1 | 7/2015 | Johansen et al. |
| 2015/0290144 | A1 | 10/2015 | Johansen |

FOREIGN PATENT DOCUMENTS

| EP | 0418680 A2 | 3/1991 |
| JP | H06-32773 A | 2/1994 |
| JP | 2010-202608 A | 9/2010 |
| WO | 1998/03164 A1 | 1/1998 |
| WO | 02/100991 A2 | 12/2002 |
| WO | 2004/052310 A2 | 6/2004 |
| WO | 2010/008299 A1 | 1/2010 |

OTHER PUBLICATIONS

C. Ferrell et al. "Trans Fatty Acids in Membranes: The Free Radical Path", (2007) Mol. Biotech. 37:19-25.
Mengele, E.A et al. "Effects of Oxygen and Antioxidants on the cis-trans-Isomerization of Unsaturated Fatty Acids caused by Thiyl Radicals", (2010) Mos. Univ. Chemistry Bull 65: 210-211.
Klein, E and N. Weber "In Vitro Testfor the Effectiveness of Antioxidants as Inhibitors of Thiyl Radical-Induced Reactions with Unsaturated Fatty Acids", (2001) J. Agric. Food Chem. 49: 1224-1227.
Huwiler, A et al. "The w3-polyunsaturated fatty acid derivatives AVX001 and AVX002 directly inhibit cytosolic phospholipase A2 and suppress PGE2 formation in mesangial cells", (2012) Br. J. Pharm. 167: 1691-1701.
Holmeide, A and L. Skattebol, "Syntheses of some polyunsaturated trifluoromethyl ketones as potential phospholipase A2 inhibitors", (2000) J. Chem. Soc. Perkin Trans. 1: 2271-2276.
But, T and P. Toy, "The Mitsonobu Reaction: Origin, Mechanism, Improvements, and Applications", (2007) Chem. Asian J. 2: 1340-1355.
Swamy, K.C et al.,Mitsonobu and Related Reactions: Advances and Applications (2009) Chem. Rev. 109: 2551-2651.
Chatgilialoglu, C et al., "Geometrical isomerism of Monounsaturated Fatty Acids: Thiyl Radical Catalysis and Influence of Antioxidant Vitamins", (2002) Free Rrad. Biology & Medicine, 33: 1681-1692.
Hung, W-L, et al., "Inhibitor Activity of Natural Occuring Antioxidants on Thiyl Radical-Induced trans-Arachidonic Acid Formation", (2011) J. Agric. Food Chem. 1968-1973.
English Language Summary of First Office Action issued in Counterpart Chinese Application No. 2014800449786, dated Jul. 28, 2016 (9 Pages).

*Primary Examiner* — Joseph R Kosack
(74) *Attorney, Agent, or Firm* — McCarter & English, LLP; Steven G. Davis

(57) ABSTRACT

The invention relates to the manufacture of certain polyunsaturated compounds employing a particular application of the Mitsonobu reaction in the presence of at least one anti-oxidant. We have found a method of making a pharmaceutically-acceptable polyunsaturated ester or thioester compound directly, which can ultimately be converted to the advantageous ketone compounds, in which unwanted oxidation and cis/trans isomerization are substantially reduced or eliminated using particular Mitsonobu chemistry.

27 Claims, 8 Drawing Sheets

HPLC chromatogram showing outcome of Experiment 2 (without area%)

HPLC chromatogram showing outcome of Experiment 2 (with area%)

HPLC chromatogram showing outcome of Experiment 3 (without area%)

HPLC chromatogram showing outcome of Experiment 3 (with area%)

HPLC chromatogram showing outcome of Experiment 4 (with area%)

HPLC chromatogram showing outcome of Experiment 5 (with area%)

PROCESS FOR THE PREPARATION OF A POLYUNSATURATED KETONE COMPOUND

CROSS-REFERENCES TO RELATED APPLICATIONS

This application is a 35 U.S.C. § 371 U.S. national entry of International Application PCT/EP2014/065853 (WO 2015/011206 A1) having an International filing date of Jul. 23, 2014, which claims under 35 U.S.C. § 119 the benefit of United Kingdom Patent Application No. 1313238.6, filed Jul. 24, 2013. The entire contents of both applications are incorporated herein by reference in their entirety.

FIELD OF THE INVENTION

The invention generally relates to a method of making a polyunsaturated ester or thioester compound. The invention further relates to conversion of the thioester to its corresponding thiol and conversion of that thiol to a polyunsaturated ketone. More particularly, the invention relates to a process for the preparation of a polyunsaturated thioester and hence also the subsequent thiol and polyunsaturated ketone compound in which unwanted oxidation and cis/trans isomerism reactions are substantially reduced or eliminated during the synthesis.

BACKGROUND

Many biologically active polyunsaturated fatty acids have one or more carbon-carbon double bonds in the cis configuration. Free radicals have been reported to support isomerization of these bonds to a less desirable trans configuration. Cis/trans isomerization can adversely effect polyunsaturated compounds intended for pharmaceutical use, for example, by reducing biological activity, and/or complicating synthesis. See, for example, C. Ferreri et al. (2007) *Mol. Biotech.* 37:19; Chatgilialoglu, C et al. (2002) *Free Rrad. Biology & Medicine,* 33: 1681; and WO 2002/100991.

Some, but not all, free radicals have been reported to support cis/trans isomerism of particular polyunsaturated compounds. It is believed that the kinetics of radical-mediated oxidation depend on several parameters including the chemical nature of the unsaturated compound to be made, temperature, pH, presence or absence of light, oxygen, etc. Free radicals have been reported to occur naturally in the environment or as unwanted by-products that are produced from certain chemical reactions. See, for example, Mengele, E. A et al. (2010) *Mos. Univ. Chemistry Bull* 65: 210.

There have been attempts to reduce oxidation and cis/trans isomerism of carbon-carbon double bonds. In one approach, an antioxidant such as octyl gallate, ascorbic acid, a polyphenol, mercaptoethanol, beta-carotene, or 2,6,-di-tert-butyl-4-methylphenol (BHT), for example, is added to reduce unwanted oxidation reactions. See Mengele, E. A, ibid; Klein, E and N. Weber (2001) *J. Agric. Food Chem.* 49: 1224; and Hung, W-L, et al. (2011) *J. Agric. Food Chem.* 1968.

There have been reports that certain polyunsaturated trifluoromethyl ketone compounds have useful biological activities. See, for example, U.S. Pat. No. 7,687,543; Huwiler, A et al. (2012) *Br. J. Pharm.* 167: 1691.

Methods for preparing particular polyunsaturated ketones have been disclosed. In one method disclosing the synthesis of particular polyunsaturated trifluoromethyl ketones, a Mitsunobu-type reaction was used to transform an alcohol to the corresponding thioester. Further chemical reactions were said to produce the polyunsaturated trifluoromethyl ketone (compound 18 therein) in 71% yield. See Holmeide, A and L. Skattebol (2000) *J. Chem. Soc. Perkin Trans.* 1: 2271.

There is general recognition that a compound intended for pharmaceutical use should be produced in high yield, e.g. 70% or more. Less than satisfactory yields can be associated with unwanted side products. These can be costly or difficult to remove from the main product (API), thereby making further pharmaceutical development difficult. Additionally, regulatory agencies often require a detailed analysis of side products in compounds intended for pharmaceutical use. This requirement can make scale-up costs prohibitive.

The Mitsunobu reaction is reported to involve the addition of a new functional group, often an ester, to a primary or secondary alcohol using, among other reagents, a phosphine and an azodicarboxylate. The mechanism of reaction is reported to be complex and there is controversy about the identity of the reaction intermediates. See, for example, But, T and P. Toy (2007) *Chem. Asian J.* 2: 1340; and Swamy, K. C et al. (2009) *Chem. Rev.* 109: 2551. This makes the outcome of certain Mitsonobu reactions difficult to predict.

In many instances, a Mitsunobu reaction is conducted by mixing the alcohol, carboxylic acid reactant and phosphine together in solvent at low temperature. Next, the azodicarboxylate is usually added and the reaction stirred for several hours to allow the carboxylic acid to react with the alcohol to form an ester. The present inventors have found that this process gives impurities in the context of the polyunsaturated compounds of the invention. For example, this reaction order often leads to unwanted oxidation, and/or cis/trans isomerism and leads to clear impurity peaks on HPLC.

The present inventors seek a process for the manufacture of a polyunsaturated ester or thioester and eventually a corresponding polyunsaturated ketone that produces, after suitable purification, a pharmaceutical grade compound with minimal oxidation and cis/trans isomerization by products.

SUMMARY OF INVENTION

The present inventors have found that use of the Mitsonobu reaction does not conventionally provide a polyunsaturated ketone having purity and yields sufficient for pharmaceutical use. However, the present inventors have surprisingly found that Mitsonobu chemistry can be used to make the particular compounds disclosed herein suitable for pharmaceutical use if a particular reaction order is employed and in the presence of at least one anti-oxidant. More specifically, we have found a method of making a pharmaceutically-acceptable polyunsaturated ester or thioester compound directly, which can ultimately be converted to the advantageous ketone compounds discussed herein, in which unwanted oxidation and cis/trans isomerization are substantially reduced or eliminated. Practice of the invention methods can be used to produce a variety of polyunsaturated ketone compounds suitable for pharmaceutical use including those specified herein.

It is therefore an object of the invention to prepare pharmaceutically-acceptable polyunsaturated ester or thioester compounds, which can ultimately be converted to the advantageous ketone compounds discussed herein, in which unwanted oxidation and cis/trans isomerization are substantially reduced or eliminated. The method of the invention involves conversion of an alcohol to an ester or more preferably a thioester using particular Mitsonobu chemistry in the presence of an anti-oxidant.

It is also an object of the invention to provide the target compounds in high purity, such as that which is often required by regulatory authorities. It is proposed that this can be achieved, in the context of the Mitsonobu reaction, by deprotonating essentially all of the thioacid or acid nucleophile in the reaction before addition of the polyunsaturated alcohol. It is also believed that the foregoing beneficial effects can often be amplified by combining the polyunsaturated alcohol with at least one pharmaceutically-acceptable anti-oxidant prior to addition of the alcohol to the nucleophile. Surprisingly, the presence of the anti-oxidant does not affect the success of the Mitsonobu chemistry.

Preferably, subsequent steps towards the formation of the polyunsaturated ketone are also performed in the presence of the same or a different pharmaceutically acceptable anti-oxidant so as to minimize potential for oxidation or cis/trans isomerization in subsequent reactions.

It is also within the scope of the invention if the polyunsaturated alcohol used is prepared via contact of a polyunsaturated aldehyde with a suitable electrophilic reducing agent under conditions sufficient to make the polyunsaturated alcohol. It is again believed that use of mild electrophilic reducing agents reduces unwanted reduction of double bonds, thereby helping the overall synthesis achieve better purity.

Thus, viewed from one aspect the invention provides a process for the preparation of an polyunsaturated ester or thioester comprising:

(1) combining, in a first vessel, a carboxylic acid or thioacid in the presence of a phosphine and an azodicarboxylate compound under conditions that deprotonate essentially all of the carboxylic acid or thioacid therein;

(2) combining, in a second vessel, a polyunsaturated alcohol and at least one pharmaceutically acceptable anti-oxidant; and (3) mixing the contents of the first and second vessels so as to form said polyunsaturated ester or thioester.

Viewed from another aspect the invention provides a process for the preparation of an polyunsaturated thiol comprising:

(1) combining, in a first vessel, a polyunsaturated thioacid in the presence of a phosphine and an azodicarboxylate compound under conditions that deprotonate essentially all of the thioacid therein;

(2) combining, in a second vessel, a polyunsaturated alcohol and at least one pharmaceutically acceptable anti-oxidant;

(3) mixing the contents of the first and second vessels so as to form said polyunsaturated thioester; and (4) adding at least one pharmaceutically-acceptable anti-oxidant to the polyunsaturated thioester of step (3), which may be the same or different from the anti-oxidant used in step (2), and reducing the thioester from step (3) under conditions sufficient to make a polyunsaturated thiol.

Viewed from another aspect the invention provides a process for the preparation of an polyunsaturated ketone compound comprising:

(1) combining, in a first vessel, a polyunsaturated thioacid in the presence of a phosphine and an azodicarboxylate compound under conditions that deprotonate essentially all of the thioacid therein;

(2) combining, in a second vessel, a polyunsaturated alcohol and at least one pharmaceutically acceptable anti-oxidant;

(3) mixing the contents of the first and second vessels so as to form said polyunsaturated thioester;

(4) adding at least one pharmaceutically-acceptable anti-oxidant to the polyunsaturated thioester of step (3), which may be the same or different from the anti-oxidant used in step (2), and reducing the thioester from step (3) under conditions sufficient to make a polyunsaturated thiol; and (5) reacting said polyunsaturated thiol with a compound (LG)$R^3$COX wherein X is an electron withdrawing group and $R^3$ is an alkylene group carrying a leaving group (LG), (such as LG-CH$_2$-forming

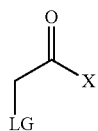

where X is an electron withdrawing group and LG is a leaving group) optionally in the presence of further added antioxidant, so as to form a polyunsaturated ketone compound, ideally of formula (II) as herein defined.

Viewed from another aspect the invention provides the product of a process as hereinbefore defined.

Viewed from another aspect the invention provides a method for producing pharmaceutically acceptable 1,1,1-trifluoro-3-(((2E,6Z,9Z,12Z,15Z,)-octadeca-2,6,9,12,15-pentaein-1-yl)thio)propan-2-one, the method comprising the steps of:

A) combining, in a first vessel, triphenylphosphine, diisopropyl azodicarboxylate (DIAD) and thioacetic acid in solvent to form a mixture and reacting the mixture, preferably at between 0-5° C. for between about 10-60 minutes, to allow complete deprotonation to occur;

B) combining, in a second vessel, (2E, 6Z, 9Z, 12Z, 15Z)-octadeca-2,6,9,12,15-pentaen-1-ol and (+/−)-α-tocopherol;

C) mixing the contents of the first and second vessels, preferably for between 10 minutes to 1 hour, to make S-((2E, 6Z, 9Z, 12Z ,15Z,)-octadeca-2,6,9,12,15-pentaein-1-yl) ethanethioate;

D) subjecting the ester produced in Step C) to dry-flash chromatography under conditions that purify the ester to at least 90% purity as determined by HPLC (% area);

E) contacting the purified ester produced in Step D) with potassium carbonate and (+/−)-α-tocopherol under conditions that reduce the ester group and produce the corresponding thiol (2E, 6Z, 9Z, 12Z, 15Z)-octadeca-2,6,912,15-pentaene-1-thiol);

F) contacting the thiol produced in step E) with 3-bromo-1,1,1-trifluoroacetone under conditions that produce the ketone

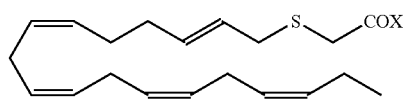

where X is CF$_3$; and

G) purifying the crude ketone produced in step F by dry-flash chromatography under conditions that purify the ketone to at least 90% purity as determined by HPLC (% area).

Viewed from another aspect the invention provides a method of producing a pharmaceutically acceptable 1,1,1- trifluoro-3-(((3Z,6Z,9Z,12Z,15Z)-octadeca-3,6,9,12,15-pentaen-1-yl)thio)propan-2-one comprising the following steps:

A) combining, in a first vessel, triphenylphosphine, diisopropyl azodicarboxylate (DIAD) and thioacetic acid in solvent to form a mixture and reacting the mixture, preferably at between 0-5° C. for between about 10-60 minutes, to allow complete deprotonation to occur;

B) combining, in a second vessel, (3Z,6Z,9Z,12Z,15Z)-octadeca-3,6,9,12,15-pentaen-1-ol and (+/−)-α-tocopherol;

C) mixing the contents of the first and second vessels, preferably for between 10 minutes to 1 hour, to make S-((3Z,6Z,9Z,12Z,15Z)-octadeca-3,6,9,12,15-pentaen-1-yl) ethanethioate;

D) subjecting the ester produced in Step C) to dry-flash chromatography under conditions that purify the ester to at least 90% purity as determined by HPLC (% area);

E) contacting the purified ester produced in Step D) with potassium carbonate and (+/−)-α-tocopherol under conditions that reduce the ester group and produce the corresponding thiol (3Z,6Z,9Z,12Z,15Z)-octadeca-3,6,9,12,15-pentaene-1-thiol;

F) contacting the thiol produced in step E) with 3-bromo-1,1,1-trifluoroacetone under conditions that produce crude

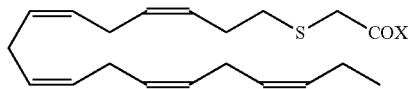

where X is CF$_3$; and

G) purifying the crude ketone produced in step F by dry-flash chromatography under conditions that purify the ketone to at least 90% purity as determined by HPLC (% area).

In any process of the invention, it is further preferred if the polyunsaturated alcohol is obtained by reduction of its corresponding aldehyde in the presence of an electrophilic reducing agent such as DIBAH.

Viewed from another aspect the invention provides a pharmaceutical composition comprising the product of a process as hereinbefore defined and at least one pharmaceutically acceptable excipient.

DEFINITIONS

The term polyunsaturated ester or polyunsaturated thioester refers to compounds which contains a hydrocarbon chain containing multiple double bonds and, of course, an ester or thioester group.

A polyunsaturated alcohol refers to a compound which contains a hydrocarbon chain containing multiple double bonds and, of course, an alcohol.

A polyunsaturated ketone refers to a compound which contains a hydrocarbon chain containing multiple double bonds and, of course, a ketone.

Thioacids are compounds containing the group —CO—SH. The carboxylic acid or thioacids used in step (1) of the process of the invention are generally low Mw compound having a Mw of 250 g/mol or less.

Generally, any polyunsaturated ketone of the invention will have an Mw of less than 500 g/mol, preferably 450 g/mol or less, more preferably 400 g/mol or less.

The term "pharmaceutically acceptable" means that which is useful in preparing a pharmaceutical that is generally non-toxic and is not biologically undesirable and includes that which is acceptable for veterinary use and/or human pharmaceutical use.

DETAILED DESCRIPTION OF INVENTION

Figure 1:
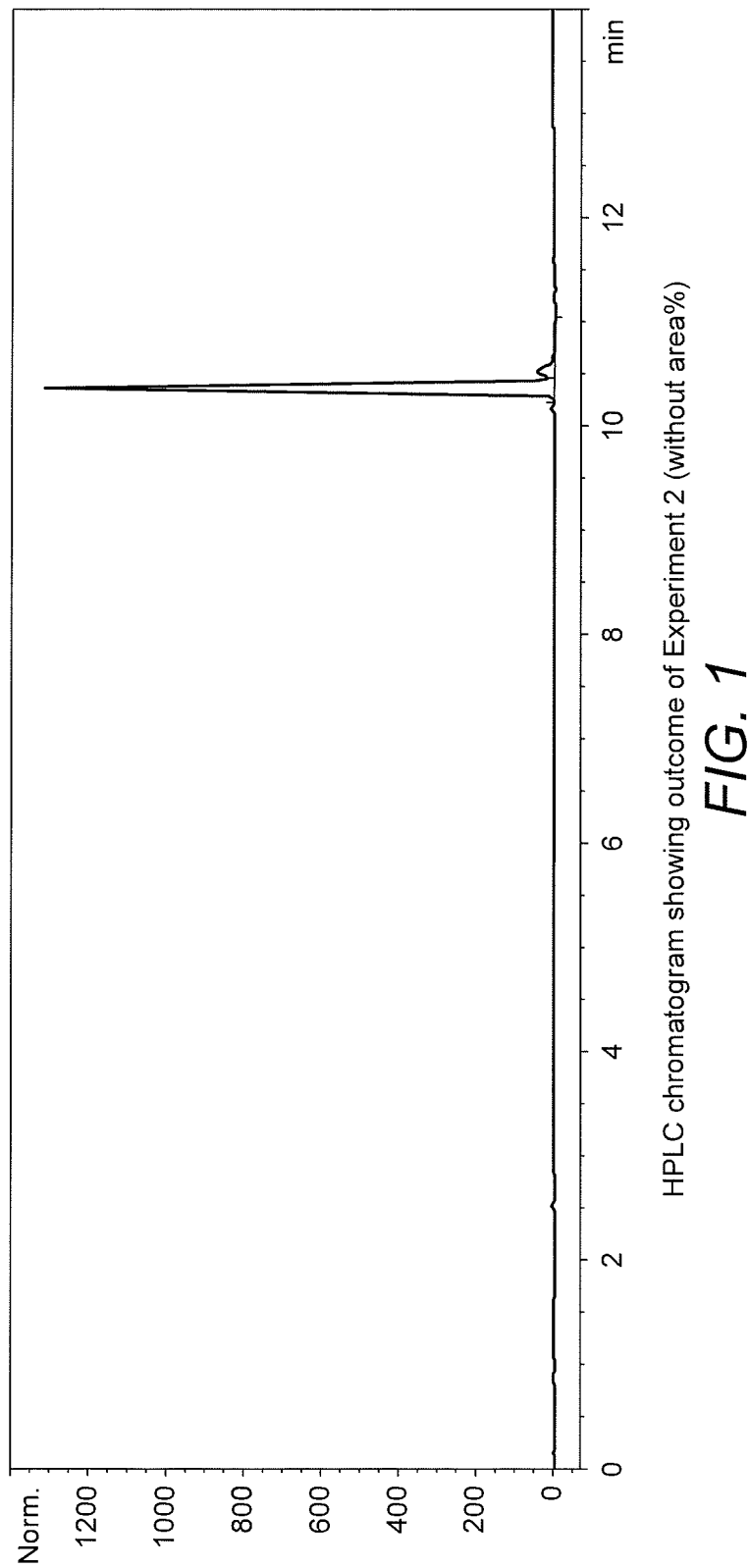
FIG. 1: HPLC chromatogram showing outcome of Experiment 2 (without area %)

This invention relates to a process for the manufacture of a polyunsaturated ester or thioester and ultimately a polyunsaturated thiol and polyunsaturated ketone. The process offers high yields and high purity. In particular, it is envisaged that after suitable purification the process steps of the invention provide the target compounds in pharmaceutical grade.

The invention provides a way of making a polyunsaturated ester or thioester, reduction of any thioester to form a thiol and subsequent conversion of that thiol to a ketone under conditions that provide the compounds in yields and purities that are often required by regulatory authorities. For example, and without wishing to be bound by theory, it is believed that production of unwanted oxidation products in the step (3), above, can be decreased or even eliminated by deprotonating and hence consuming essentially all of the acid/thioacid in step (1) before addition of the polyunsaturated alcohol in step (2). Accordingly, the mixing step (3) occurs after the reaction of essentially all of the acid/thioacid in the first step (1).

The starting material in the process of the invention, used in step (2), is a polyunsaturated alcohol. Preferably that alcohol is of formula (I)

wherein R is an optionally substituted C$_{9-23}$ unsaturated hydrocarbon group optionally interrupted by one or more heteroatoms or groups of heteroatoms selected from S, O, N, SO, SO$_2$, said hydrocarbon group comprising at least 2, preferably at least 4 double bonds.

It is preferred if in any group R, double bonds are not conjugated. The group R preferably comprises 5 to 9 double bonds, preferably 5 or 8 double bonds, e.g. 5 to 7 double bonds such as 5 or 6 double bonds.

It is also preferred if the double bonds do not conjugate with the hydroxyl group.

The double bonds present in the group R may be in the cis or trans configuration however, it is preferred if the majority of the double bonds present (i.e. at least 50%) are in the cis configuration. In further advantageous embodiments all the double bonds in the group R are in the cis configuration or all double bonds are in the cis configuration except the double bond nearest the OH group which may be in the trans configuration.

The group R may have between 9 and 23 carbon atoms, preferably 11 to 19 carbon atoms, especially 16 to 18 carbon atoms. Carbon atoms are preferably linear in the R group.

Whilst the R group can be interrupted by at least one heteroatom or group of heteroatoms, this is not preferred and the R group backbone preferably contains only carbon atoms.

The R group may by optionally substituted, e.g. carry up to three substituents, e.g. selected from halo, $C_{1-6}$ alkyl e.g. methyl, $C_{1-6}$ alkoxy. If present the substituents are preferably non-polar, and small, e.g. a methyl group. It is preferred however, if the R group remains unsubstituted.

The R group is preferably linear, i.e. there are no branches in the R chain. It preferably derives from a natural source such as a long chain fatty acid or ester. In particular, the R group may derive from arachidonic acid, docosahexaenoic acid or eicosapentaenoic acid.

It may be therefore that the polyunsaturated alcohol of use in the invention derives from a corresponding fatty acid or aldehyde (as described below in scheme 1). We have further found that when the polyunsaturated alcohol derives from its corresponding aldehyde, that polyunsaturated alcohol is preferably obtained in a reaction that involves contacting a polyunsaturated aldehyde with a suitable electrophilic reducing agent under conditions sufficient to make the polyunsaturated alcohol. Without wishing to be bound to any theory, it is believed that use of mild electrophilic reducing agents reduce unwanted reduction of double bonds, thereby helping the overall synthesis achieve better yields and purity.

The use of diisobutylaluminium hydride (DIBAH) is particularly preferred in this regard. The present inventors have surprisingly found that some other well known reducing agents such as sodium borohydride cannot be used successfully in this reduction as they increase the number of impurities formed. It is surprising that the use of DIBAH seems to reduce isomerism and hence minimises impurity formation.

The first step of the process of the invention involves Mitsonobu chemistry. This reaction typically involves dissolution of the alcohol, the carboxylic acid, and triphenylphosphine in solvent followed by addition the azodicarboxylic acid dissolved in solvent. Such a process however, does not work in the present case.

We propose a variation to the reaction order in order to avoid oxidation and/or isomerisation in the context of the compounds of the invention. It is surprising that the reaction order we use offers us the opportunity to prepare our target compounds without significant isomerisation or oxidation. Accordingly, it was unclear until our invention, that the particular reaction order we employ would solve the problem of unwanted oxidation and cis trans isomerisation. Moreover, it is even more surprising that the reaction order we employ is functional in the presence of the anti-oxidant.

Any azodicarboxylate and phosphine compound known for use in the Mitsonobu reaction can be used herein. Phosphines are a group of well known organophosphorus compounds with the formula R'$_3$P (R=organic derivative, typically an alkyl, aryl or heteroaryl group). Azodicarboxylates are compounds of general formula R"OOC—N═N—COO—R" where R" is an organic derivative such as an alkyl group or aryl group.

Preferred phosphines therefore include those of formula

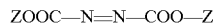

where Y is a C1-10 alkyl, C6-10 aryl, C7-12 arylalkyl, C7-12 alkylaryl, C3-10 cycloalkyl, C4-10-heteroaryl, C6-10arylO—any of which may be optionally substituted by one or more groups selected from $NH_2$, $NHR^a$ or $NR^a{}_2$ where $R^a$ is a C1-6 alkyl.

Suitable heteroaryl groups include pyridine.

Preferred phosphines for use in the invention process are triarylphosphines such as triphenylphosphine or alkylarylphosphines such as dicyclohexylphenylphosphine, diethylphenylphosphine, isopropyldiphenylphosphine, tributylphosphine, tricyclohexylphosphine, trihexylphosphine and tri-n-octylphosphine. Other phosphines of interest include 4-(dimethylamino)phenyldiphenylphosphine, diphenyl-2-pyridylphosphine and phenoxydiphenylphosphine. The use of triarylphosphines such as triphenylphosphines is especially preferred.

Preferred azodicarboxylate compounds are those of formula

ZOOC—N═N—COO—Z where each Z is independently, C1-10 alkyl, C6-10 aryl, C7-12 arylalkyl, C7-12 alkylaryl, C4-10-heteroaryl, C4-10-heterocyclic or C3-10 cycloalkyl any of which may be optionally substituted by one or more groups selected from halide. Both Z groups are preferably the same. Suitable heteroaryl groups include pyridine. Suitable heterocycles include piperidine or piperazine.

Suitable azodicarboxylate compounds are typically based on optionally substituted C1-6-alkyl esters such as diethyl azodicarboxylate (DEAD), di-tert-butyl azodicarboxylate or diisopropyl azodicarboxylate (DIAD) or optionally substituted aryl esters such as di-4-chlorobenzylazodicarboxylate. Other compounds of interest include 1,1'-(azodicarbonyl) dipiperidine.

In general therefore the nature of the phosphine and azodicarboxylate compound used in the process of the invention are not critical and any known phosphine or azadicarboxylate agent known in the literature can be used.

The polyunsaturated alcohol is reacted with an carboxylic acid or thioacid. The carboxylic acid or thioacid is generally of low molecular weight, e.g. 250 g/mol or less. The carboxylic acid or thioacid is preferably a monoacid or monothioacid. Most preferably, it is a compound $R^1COOH$ or $R^1COSH$ wherein $R^1$ is a C1-6 alkyl, C6-10 aryl group, C7-12 alkylaryl group or C7-12 arylalkyl group (such as benzyl or tolyl). Ideally $R^1$ is ethyl or Me, especially Me.

The reaction therefore of a compound R—OH as hereinbefore defined with a compound $R^1COOH$ or $R^1COSH$ in this invention yields a compound R—OCOR$^1$ or RSCOR$^1$.

Step (2) of the process of the invention requires the presence of an anti-oxidant, i.e. a compound that suppresses oxidation reactions. It is preferred if the anti-oxidant is a small molecule such as one having a molecular weight of 500 g/mol or less, such as 250 g/mol or less. The anti-oxidant should ideally be approved for use by the FDA.

The anti-oxidant used in step (2) of the process of the invention is preferably butyl hydroxyanisole, butyl hydroxytoluene, propyl gallate, tocopherol, ascorbic acid, ascorbyl palmitate, thioglycerol, thioglycolic acid, sodium bisulphite, sodium sulphite, sodium metabisulphite, edetate tetrasodium, or EDTA.

The use of tocopherol is especially preferred, particularly (+/−)-alpha-tocopherol.

It will be appreciated that the compounds of the invention are primarily for medicinal use and hence any anti-oxidant employed is preferably pharmaceutically acceptable.

The amount of antioxidant added to the polyunsaturated alcohol may be between 0.01 to 1 mol %, 0.1 to 0.5 mol % of the polyunsaturated alcohol.

It has been reported that a typical Mitsunobu reaction is complex and there is controversy regarding the identity and activity of reaction intermediates. However, the present inventors have found that consuming essentially all of the acid/thioacid before adding the polyunsaturated alcohol in step (3), above, it is possible to substantially increase yields and, most importantly, the purity of the resulting polyunsaturated ester/thioester to a level acceptable for many pharmaceutical applications. They have also learned that the presence of a pharmaceutically-acceptable anti-oxidant can be used in the present methods to help reduce unwanted cis/trans isomerization without being destroyed or otherwise blocked or inactivated by agents and conditions that are used in many Mitsunobu reactions. It is surprising that the presence of the anti-oxidant does not affect the success of the reaction. Given the uncertainty over the mechanism by which the Mitsunobu reaction actually works, there is always a question mark over whether the presence of an additional reagent such as the anti-oxidant will interfere with the numerous transient intermediate species produced in the reaction.

Typically, a 1:1:1 ratio of the reagents might be used in the Mitsonobu reaction. In the claimed process we require the use of sufficient phosphine and azodicarboxylate to deprotonate the acid or thioacid essentially completely, preferably completely. In particular therefore, there should not be an excess of acid or thioacid present. In fact, it is preferred if there is an excess of the Mitsonobu reagents used.

The reaction in step (1) can be controlled using low temperature, preferably less than 10° C., e.g. 0 to 5° C. The mixture of step (1) is ideally left for a period of 10 mins to an hour, such as at least 20 or at least 30 mins, to ensure deprotonation of the acid or thioacid to its corresponding carboxylate or thiocarboxylate ion. To ensure full deprotonation, it will be appreciated that there should be an excess of the Mitsonobu reagents present, relative to the acid or thioacetic acid.

Thus, ideally there should be at least 1.1 molar equivalents of both the phosphine and azocarboxylate reactants compared to the acid or thioacid. This should ensure full deprotonation occurs.

Ideally, the blend of phosphine, azodicarboxylate and acid/thioacid forms a solution, in particular a clear solution. There should be no material stuck to sides of the vessel in which the reaction takes place. As the deprotonation takes place rapidly, with good stirring full deprotonation should occur very rapidly (in seconds if not less) and certainly within a period of 10 mins.

If full deprotonation does not occur, this manifests itself in the final product in terms of high levels of impurity. Without full deprotonation, it is possible to observe 10 wt % or more of impurities in the final product.

It is believed that the beneficial effects in terms of purity are amplified by combining the polyunsaturated alcohol with at least one pharmaceutically-acceptable antioxidant in step (2) prior to addition of the alcohol to the step (1) reaction material. Preferably, these steps and subsequent steps to make the polyunsaturated ketone, are performed in the presence of the same or different pharmaceutically acceptable anti-oxidant so as to minimize potential for cis/trans isomerization in the reaction.

The actual reaction in step (3) of the process of the invention may take 10 mins to 1 hour and can be carried out at any convenient temperature, e.g. ambient temperature.

It will be appreciated that typically the molar amount of polyunsaturated alcohol is stoichiometric with the amount of acid or thioacid present. Once the thioester or ester has been formed it can be worked up conventionally, e.g. subjected to dry-flash chromatography. Ideally, the ester or thioester should have a purity of at least 90% as determined by HPLC (% area) at this point. More preferably purity should be 91% or more, such as 92% or more, ideally 93% or more, especially 94% or even 95% or more.

The process herein has been found to produce the ester or thioester in high yield, e.g. 70% or more. Also, as we show in our examples, that we can eliminate the presence of impurities detectable on HPLC.

In a preferred embodiment, the thioester formed in the process of the invention is then itself converted to its corresponding thiol. Whilst this can in theory be carried out using any conventional reduction process, e.g. using diisobutylaluminium hydride, in order to avoid side reaction, impurity formation and cis-trans isomerisation of double bonds present, the inventors propose carrying out this reaction in the presence of an anti-oxidant. The anti-oxidant is preferably added at this stage although in theory, if there is residual anti-oxidant from the formation of the thioester then no further anti-oxidant may be needed. Typically however, any anti-oxidant added during formation of the thioester is removed during purification of that thioester and hence further anti-oxidant is needed.

That anti-oxidant can be the same or different from the one added in step (2) of the process above. The antioxidant is preferably selected from butyl hydroxyanisole, butyl hydroxytoluene, propyl gallate, tocopherol, ascorbic acid, ascorbyl palmitate, thioglycerol, thioglycolic acid, sodium bisulphite, sodium sulphite, sodium metabisulphite, edetate tetrasodium, or EDTA.

The use of tocopherol is especially preferred. The amount of anti-oxidant added/present may again by of the order of 0.01 to 1 mol %, preferably 0.1 to 0.5 mol % relative to the amount of polyunsaturated thioester present.

Also, the foregoing beneficial effects can be further enhanced by making the polyunsaturated thiol in a reaction that involves contacting a polyunsaturated thioester with a suitable mild electrophilic reducing agent under conditions sufficient to make the polyunsaturated thiol. Without wishing to be bound to any theory, it is believed that use of mild electrophilic reducing agents, as discussed below, reduce unwanted reduction of double bonds, thereby helping the overall synthesis achieve better yields and purity.

Suitable reducing agents are ideally metal carbonates such as potassium carbonate. The use of a solvent such as methanol is appropriate.

Thus, according to a further aspect, the invention provides a process for the preparation of making a pharmaceutically-acceptable polyunsaturated thiol which method includes:

(1) combining, in a first vessel, a thioacid in the presence of a phosphine and an azodicarboxylate compound under conditions that deprotonate essentially all of the thioacid therein;

(2) combining, in a second vessel, a polyunsaturated alcohol and at least one pharmaceutically acceptable anti-oxidant; and (3) mixing the contents of the first and second vessels under conditions sufficient to make the corresponding polyunsaturated thioester; and (4) contacting the polyunsaturated thioester with a second pharmaceutically acceptable anti-oxidant and reacting the resulting mixture under conditions sufficient to make the polyunsaturated thiol.

Preferred thioesters are therefore of formula R—SCOR[1] where R and R[1] are as hereinbefore defined. Preferred thiols are simply RSH.

Ideally, the thiol should have a purity of at least 90% as determined by HPLC (% area) at this point. More preferably purity should be 91% or more, such as 92% or more, ideally 93% or more, especially 94% or even 95% or more.

The process herein has been found to produce the thiol in high yield, e.g. 70% or more. Also, as we show in our examples, we can eliminate the presence of impurities detectable on HPLC.

Ideally of course, the process of the invention targets a variety of pharmaceutically-acceptable polyunsaturated ketones that are suitable for pharmaceutical use. Preferred compounds include a ketone group comprising an electron withdrawing group and a sulphur atom in the α, β, γ, or δ position from the ketone group. An electron withdrawing group or EWG draws electrons away from a reaction centre.

Preferred polyunsaturated ketone targets of the invention are therefore of formula (II)

$$R^2—CO—X \quad (II)$$

wherein $R^2$ is a $C_{10-24}$ polyunsaturated hydrocarbon group interrupted α, β, γ, or δ position from the ketone group by a S atom; and X is an electron withdrawing group (EWG).

Suitable electron withdrawing groups X for any compound of the invention are CN, phenyl, CHal$_3$, CHal$_2$H, CHalH$_2$ wherein Hal represents a halogen, especially F. The EWG is especially CHal$_3$, e.g. CF$_3$.

It is most preferred if the S atom is beta to the carbonyl.

It is preferred if in any group $R^2$, double bonds are not conjugated. The group $R^2$ preferably comprises 5 to 9 double bonds, preferably 5 or 8 double bonds, e.g. 5 to 7 double bonds such as 5 or 6 double bonds.

It is also preferred if the double bonds do not conjugate with the hydroxyl group.

The double bonds present in the group $R^2$ may be in the cis or trans configuration however, it is preferred if the majority of the double bonds present (i.e. at least 50%) are in the cis configuration. In further advantageous embodiments all the double bonds in the group $R^2$ are in the cis configuration or all double bonds are in the cis configuration except the double bond nearest the S group which may be in the trans configuration.

The group $R^2$ may have between 10 and 24 carbon atoms, preferably 12 to 20 carbon atoms, especially 17 to 19 carbon atoms.

In a preferred embodiment, the invention provides a method of producing a pharmaceutically acceptable 1,1,1-trifluoro-3-(((2E,6Z,9Z,12Z,15Z,)-octadeca-2,6,9,12,15-pentaein-1-yl)thio)propan-2-one (see also scheme 1 herein):

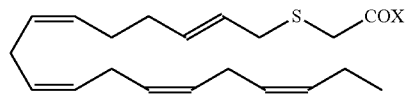

where X is CF$_3$; or related compound

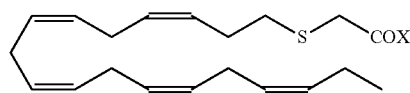

where X is CF$_3$.

The last step of the process of the invention therefore involves reaction of the thiol with a suitable ketone to form the desired compounds of formula (II). The reacting ketone compound is preferably of formula (LG)R$^3$CO—X where $R^3$ taken together with the R group of the polyunsaturated alcohol used in step (2) forms the group $R^2$ in formula (II), i.e.

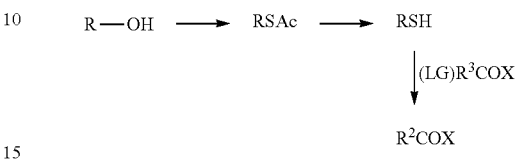

$R^3$ is preferably C1-3-alkylene, such as methylene. LG represents a leaving group which is nucleophilicly substituted by the thiol group. A leaving group is a molecular fragment that departs with a pair of electrons in heterolytic bond cleavage. Preferably of course, (LG)R$^3$—COX represents the compound LG-CH$_2$—COX, where LG is a leaving group such as a halide, tosyl, mesyl and so on. Ideally LG is a halide such as Br. X is an electron withdrawing group as hereinbefore defined in the above formulae, preferably CF$_3$ again. Most preferably (LG)R$^3$—COX is BrCH$_2$—COCF$_3$.

This final reaction step may take place in the presence of further anti-oxidant as hereinbefore defined. Again, anti-oxidant might inherently be present as carry over from the thioester reduction step and in that scenario, it may not be necessary to add more anti-oxidant. It is within the scope of the invention however, to add more anti-oxidant, e.g. where the thiol formed was purified and hence anti-oxidants removed.

The use of tocopherol is especially preferred if an anti-oxidant is employed. The amount of anti-oxidant added/present may again by of the order of 0.01 to 1 mol % preferably 0.1 to 0.5 mol % compared to the content of polyunsaturated thiol.

It will be appreciated that any reaction described herein may need to be carried out in the absence of oxygen, e.g. under an Ar atmosphere.

Ideally, the ketone should have a purity of at least 90% as determined by HPLC (% area) at this point. More preferably purity should be 91% or more, such as 92% or more, ideally 93% or more, especially 94% or even 95% or more.

The process herein has been found to produce the ketone in high yield, e.g. 70% or more. Also, as we show in our examples, we can eliminate the presence of impurities detectable on HPLC.

In a most preferred embodiment, the process of the invention includes at least the following steps:

A) combining, in a first vessel, a phosphine, an azodicarboxylate and thioacetic acid in solvent to form a mixture and allowing complete deprotonation of said thioacetic acid to occur;

B) combining, in a second vessel, (2E, 6Z, 9Z, 12Z, 15Z)-octadeca-2,6,9,12,15-pentaen-1-ol (C18 allylic alcohol) and an anti-oxidant;

C) mixing the contents of the first and second vessels to make S-((2E, 6Z, 9Z, 12Z ,15Z,)-octadeca-2,6,9,12,15-pentaein-1-yl) ethanethioate.

More specifically, the process of the invention requires the following steps;

A) combining, in a first vessel, triphenylphosphine, diisopropyl azodicarboxylate (DIAD) and thioacetic acid in solvent and allowing complete deprotonation of said thioacetic acid to occur;

B) combining, in a second vessel, (2E, 6Z, 9Z, 12Z, 15Z)-octadeca-2,6,9,12,15-pentaen-1-ol and tocopherol;

C) mixing the contents of the first and second vessels to make S-((2E, 6Z, 9Z, 12Z ,15Z,)-octadeca-2,6,9,12,15-pentaein-1-yl) ethanethioate.

It is then further preferred if the S-((2E, 6Z, 9Z, 12Z ,15Z,)-octadeca-2,6,9,12,15-pentaein-1-yl) ethanethioate is:

D) subjected to dry-flash chromatography under conditions that purify the ester to at least 90% purity as determined by HPLC (% area).

Moreover, after either step C or D, it is preferred if,

E) the optionally purified S-((2E, 6Z, 9Z, 12Z ,15Z,)-octadeca-2,6,9,12,15-pentaein-1-yl) ethanethioate produced in Step C) or D) is contacted with a metal carbonate, such as potassium carbonate, and tocopherol under conditions that reduce the ester group and produce the corresponding thiol (2E, 6Z, 9Z, 12Z, 15Z)-octadeca-2,6,912,15-pentaene-1-thiol).

It is then preferred if, F) the thiol produced in step E) is contacted with 3-bromo-1,1,1-trifluoroacetone under conditions that produce

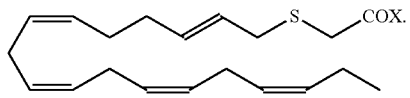

where X is $CF_3$.

That compound can be purified in by dry-flash chromatography to at least 90% purity as determined by HPLC (% area) to produce a pharmaceutically acceptable compound.

In another aspect, the invention provides a process of producing a pharmaceutically acceptable 1,1,1-trifluoro-3-(((3Z,6Z,9Z,12Z,15Z)-octadeca-3,6,9,12,15-pentaen-1-yl)thio)propan-2-one

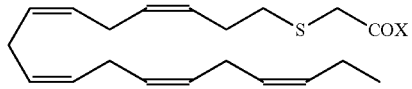

where X is $CF_3$, following the protocols above with appropriate substitution of the starting alcohol to (3Z,6Z,9Z,12Z, 15Z)-octadeca-3,6,9,12,15-pentaen-1-ol.

It will be appreciated that the compounds made in the process of the invention have a variety of applications, e.g. in the treatment of chronic inflammatory disorders. They can be formulated as pharmaceutical compositions using well known techniques. A further discussion of such techniques is not required here.

The invention will now be described with reference to the following non limiting examples and figures.

FIGS. 1 to 8 are HPLC chromatograms showing the products of the various examples below.

EXAMPLES

Example 1

Overview of 1,1,1-trifluoro-3-(((2E,6Z,9Z,12Z, 15Z,)-octadeca-2,6,9,12,15-pentaein-1-yl)thio)propan-2-one Synthesis The following information provides a general overview of the synthesis of the polyunsaturated ketone. Referring to Scheme 1, Step A and Step B are mentioned in more detail in Example 6, below.

All steps toward making the C18 allylic alcohol (Scheme 1, below) were carried out essentially as described in *J. Chem. Soc., Perkin Trans.* 1, 2000, 2271-2276 (Skattebøl and Holmeide), with one modification: instead of sodium borohydride in the reduction of aldehyde to alcohol, diisobutylaluminium hydride (DIBAH) was used to reduce overreduction of the trans double bond. During the three last steps (Scheme 1, below), the following precautions/modifications were introduced:

All reactions were carried out under an argon atmosphere. The lights in the fume hoods were to be turned off. No other precautions regarding light protection were considered necessary. In addition, the 3 last steps (called A, B and C, respectively) are performed in the presence of alpha-tocopherol. The sequence of reagent addition in the Mitsonobu reaction was considered to be important in order to avoid isomerization. It is anticipated that it is of crucial importance that all of the thioacetic acid has reacted completely prior to introduction of C18 allylic alcohol. Furthermore, both the crude and purified product of step (A) are flushed with argon capped with a septum and placed in the freezer when stored. Step (B) is carried out without purification, but again: the crude product is to be stored at −18° C. under argon atmosphere if storage is necessary. During the last step great care was taken to ensure that both the crude product and purified material was kept under argon.

Scheme 1: Overview of synthesis of 1,1,1-trifluoro-3-(((2E,6Z,9Z,12Z,15Z,)-octadeca-2,6,9,12,15-pentaein-1-yl)thio)propan-2-one

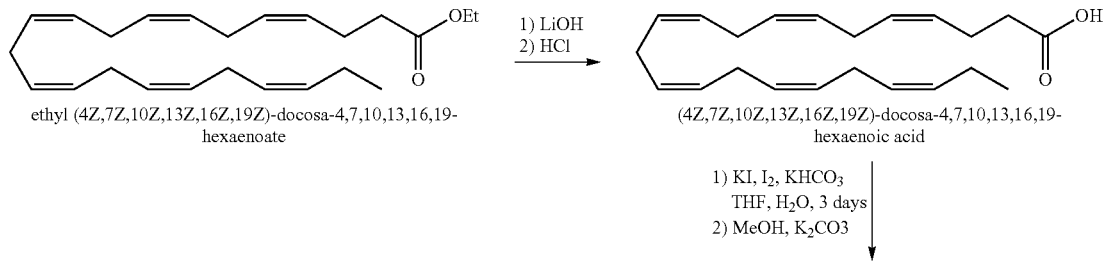

-continued

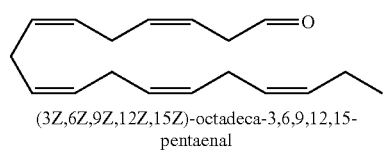
(3Z,6Z,9Z,12Z,15Z)-octadeca-3,6,9,12,15-pentaenal

1) HCOOH (1 1), Ac₂O) (150 ml)
2) LiOH, H₂O—MeOH, 0 oC
3) NaIO₄ MeOH—H₂O

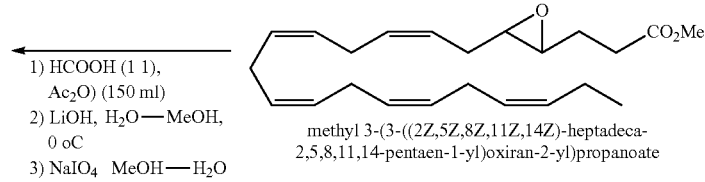
methyl 3-(3-((2Z,5Z,8Z,11Z,14Z)-heptadeca-2,5,8,11,14-pentaen-1-yl)oxiran-2-yl)propanoate DBU
Et₂O

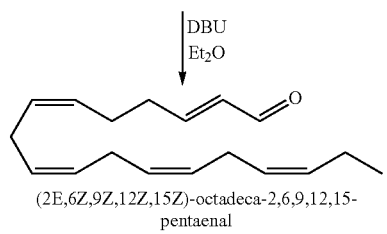
(2E,6Z,9Z,12Z,15Z)-octadeca-2,6,9,12,15-pentaenal

DIBAH
Toluene

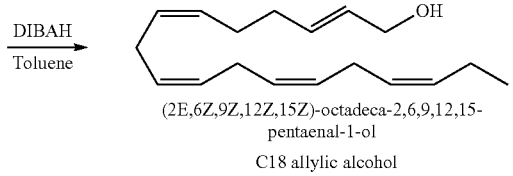
(2E,6Z,9Z,12Z,15Z)-octadeca-2,6,9,12,15-pentaenal-1-ol
C18 allylic alcohol STEP A Mitsonobu | DIAD, PPh₃ CH₃COSH

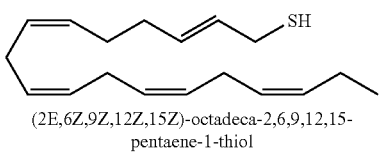
(2E,6Z,9Z,12Z,15Z)-octadeca-2,6,9,12,15-pentaene-1-thiol

STEP B
K₂CO₃
MeOH

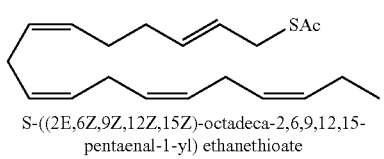
S-((2E,6Z,9Z,12Z,15Z)-octadeca-2,6,9,12,15-pentaenal-1-yl) ethanethioate

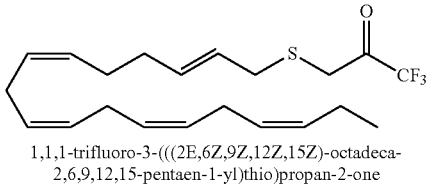
NaHCO₃
EtOH, H₂O

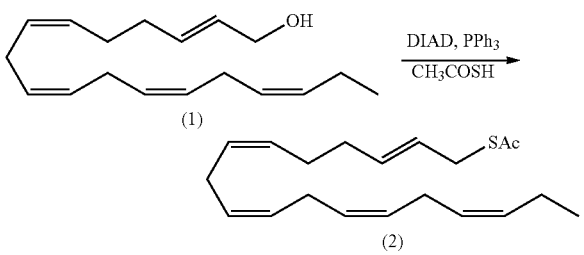
1,1,1-trifluoro-3-(((2E,6Z,9Z,12Z,15Z)-octadeca-2,6,9,12,15-pentaen-1-yl)thio)propan-2-one

Comparative Example 2

Production of Polyunsaturated Thioester Produces a Contaminant Migrating Close to the Main Product Peak

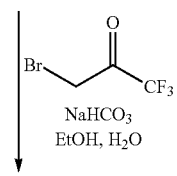
(1)

DIAD, PPh₃
CH₃COSH (2) SAc

The lights in the fume hoods were turned off. No other precautions regarding light protection were considered necessary. Under argon, the following solution was prepared in a 200 ml volumetric flask with glass stopper:

(2E,6Z,9Z,12Z,15Z)-octadeca-2,6,9,12,15-pentaen-1-ol ((1), 15.0 g, 57.6 mmol), thioacetic acid (5.00 ml, 70.0 mmol) and alpha-tocopherol (30.4 mg) were combined in dry THF (150 ml). The solution was cooled to 0° C.

In a 1 liter round bottomed flask, was placed triphenylphosphine (18.1 g, 69.1 mmol) followed by dry THF (300 ml). The flask was added a stirring bar, flushed with argon and immersed in an ice-bath with septum and stirred at 0° C. for 10 minutes. Diisopropylazodicarboxylate (13.6 ml, 57 6 mmol) was added in one portion through septum with syringe and the reaction mixture stirred for 30 minutes at 0° C. The precooled solution of (2E,6Z,9Z,12Z,15Z)-octadeca-2,6,9,12,15-pentaen-1-ol, thioacetic acid and alpha-tocopherol in dry THF was added in one portion. The cooling bath was removed and the reaction mixture stirred for one hour. The clear yellow solution was evaporated under reduced pressure (rotary evaporator) to remove THF. To the residue was added diethyl ether (120 ml) and the flask rotated on the rotary evaporator for 10 minutes at room temperature. The mixture was filtered through a glass sinter (type 3) and the residue rinsed out with ether (2×50 ml). The combined filtrate was evaporated under reduced pressure (rotary evaporator). To the residue was added heptane (100 ml) and the flask rotated 10 minutes at room temperature. Filtration through the glass sinter from above, rinsing with heptane (2×25 ml) and concentration afforded 24.8 g of the crude product as a yellow oil. Purification was performed by dry flash chromatography and flash chromatography (heptane: EtOAc gradient) to give 12.5 gram (68%) of S-((2E,6Z,9Z, 12Z,15Z)-octadeca-2,6,9,12,15-pentaen-1-yl) ethanethioate as a colorless oil.

Figure 2:
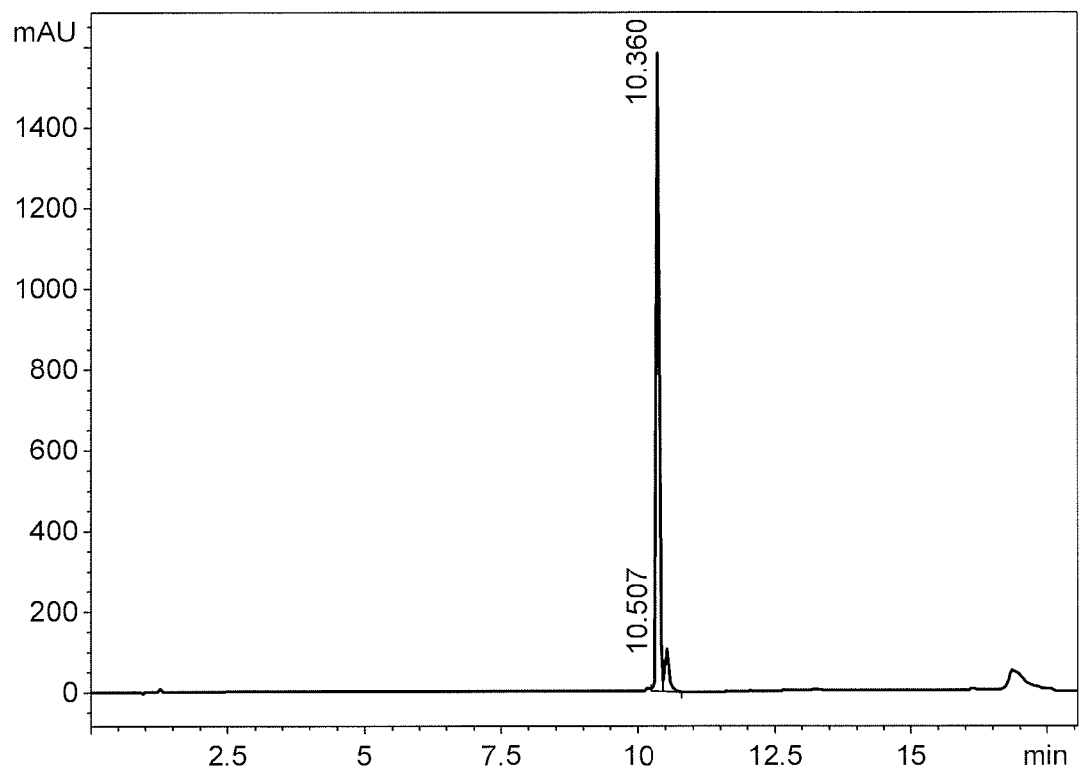
FIG. 2: HPLC chromatogram showing outcome of Experiment 2 (with area %)

FIGS. 1 and 2 show chromatograms of the product in the synthesis. The side-product can be seen as a shoulder to the immediate right of the main product peak in FIGS. 1 and 2.

Example 3

Prior Reaction of Thioacetic Acid Before Addition of the Polyunsaturated Alcohol Reduced Presence of the contaminant

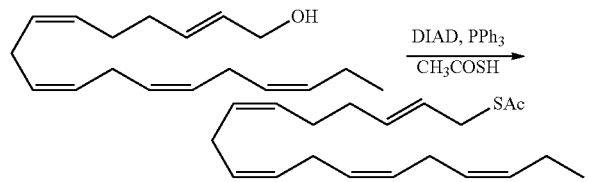

The lights in the fume hoods are to be turned off. No other precautions regarding light protection are considered necessary.

Triphenylphosphine (6.06 g, 23 1 mmol) is weighed, transferred to a 1 liter round bottom flask equipped with a magnetic stirring bar, dissolved in dry THF (300 ml), flushed with argon, capped with a septum and immersed in an ice/water bath. The solution is stirred at 0.5° C. for 11 minutes.

Diisopropyl azodicarboxylate (DIAD) (4.50 ml, 20 8 mmol) is added the reaction mixture in one portion and the mixture is stirred at 0.5° C. for 32 minutes.

Thioacetic acid (1.50 ml, 21 mmol) is added the reaction mixture in one portion and the mixture is stirred at 3.5° C. for 15 minutes.

Alpha-Tocopherol (9.8 mg) and octadeca-2(E),6(Z),9(Z), 12(Z),15(Z)-pentaen-1-ol (5.00 g, 19 2 mmol) is weighed out, transferred to an Erlenmeyer flask and dissolved in dry THF (50 mL) and added to the reaction mixture in one portion. After the addition the cooling bath is removed and the mixture is stirred for 47 minutes.

The reaction mixture is concentrated under reduced pressure. To the residue was added diethyl ether (40 ml) and the flask rotated on the rotary evaporator for 10 minutes at room temperature. The mixture was filtered through a glass sinter (type 3) and the residue rinsed out with ether (2×15 ml). The combined filtrate was evaporated under reduced pressure (rotary evaporator). To the residue was added heptane (35 ml) and the flask rotated 10 minutes at room temperature. Filtration through the glass sinter from above, rinsing with heptane (2×10 ml) and concentration afforded the crude product as a yellow oil. Purification was performed by dry flash chromatography (heptane:EtOAc gradient) to give 4.52 gram (74%) of S-((2E,6Z,9Z,12Z,15Z)-octadeca-2,6,9,12, 15-pentaen-1-yl) ethanethioate as a colorless oil.

Figure 3:
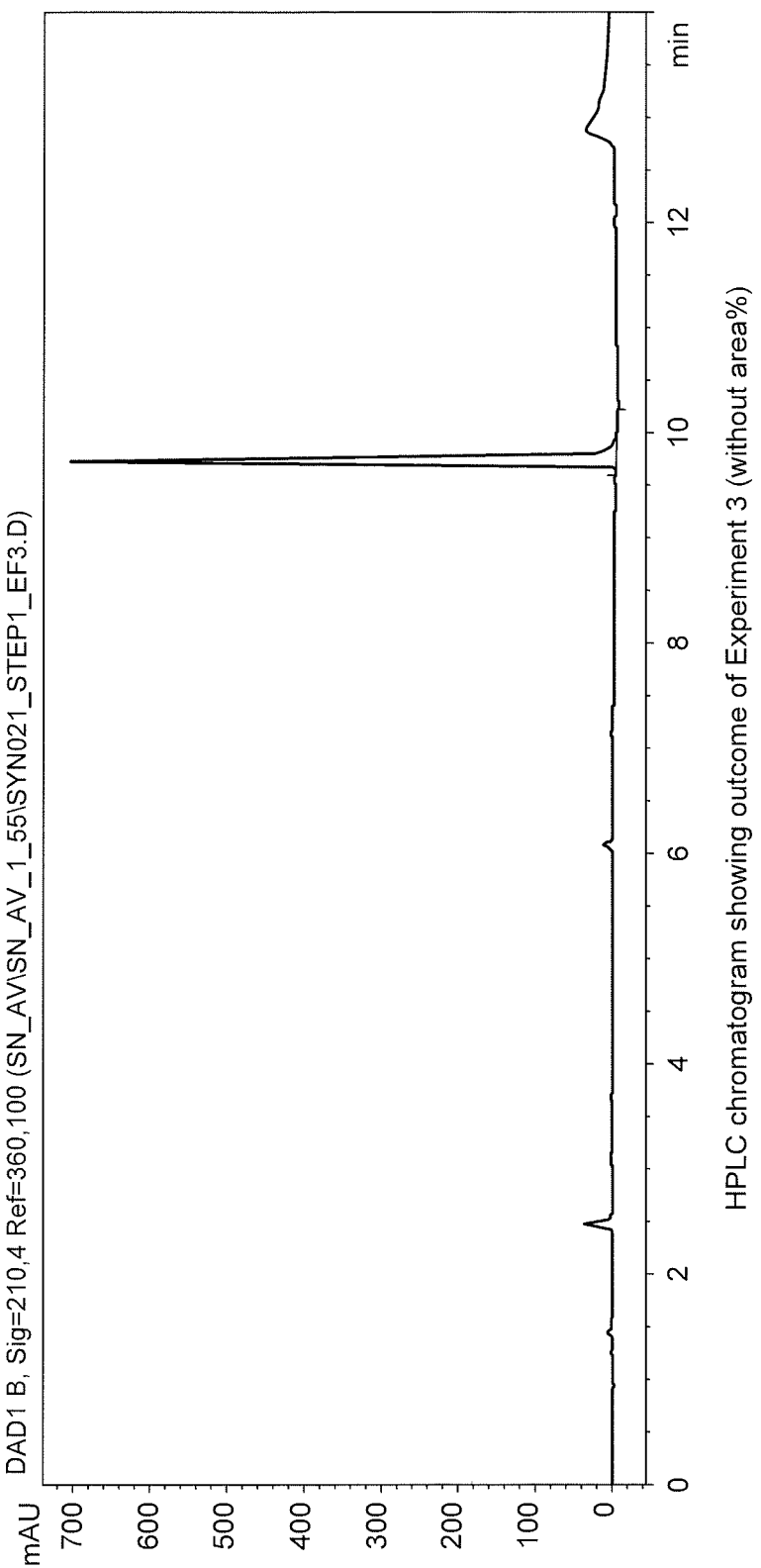
FIG. 3: HPLC chromatogram showing outcome of Experiment 3 (without area %)
Figure 4:
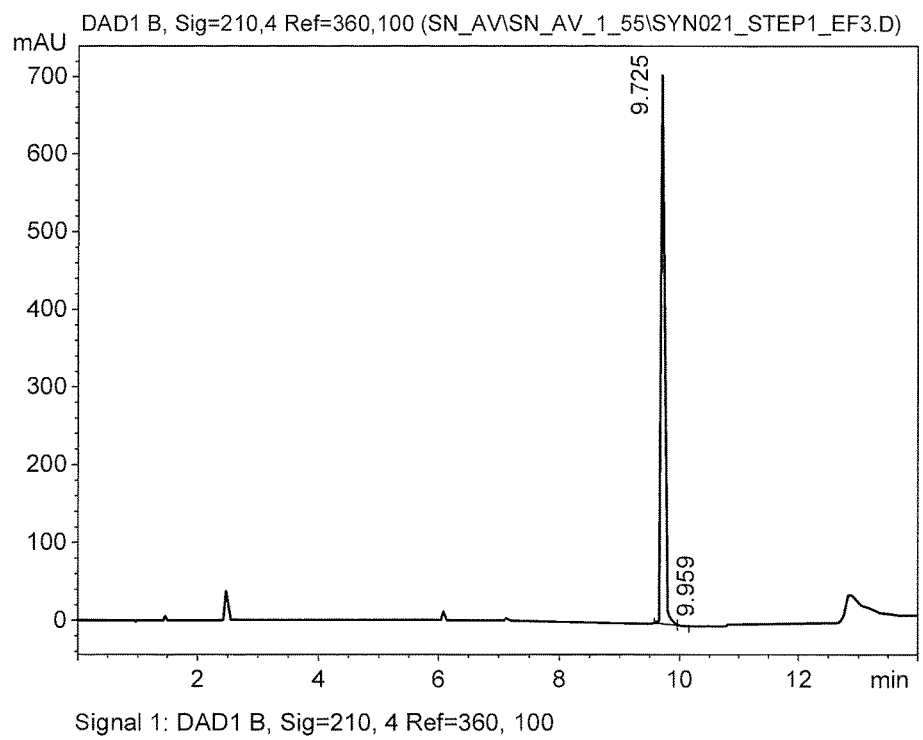
FIG. 4: HPLC chromatogram showing outcome of Experiment 3 (with area %)
Figure 5:
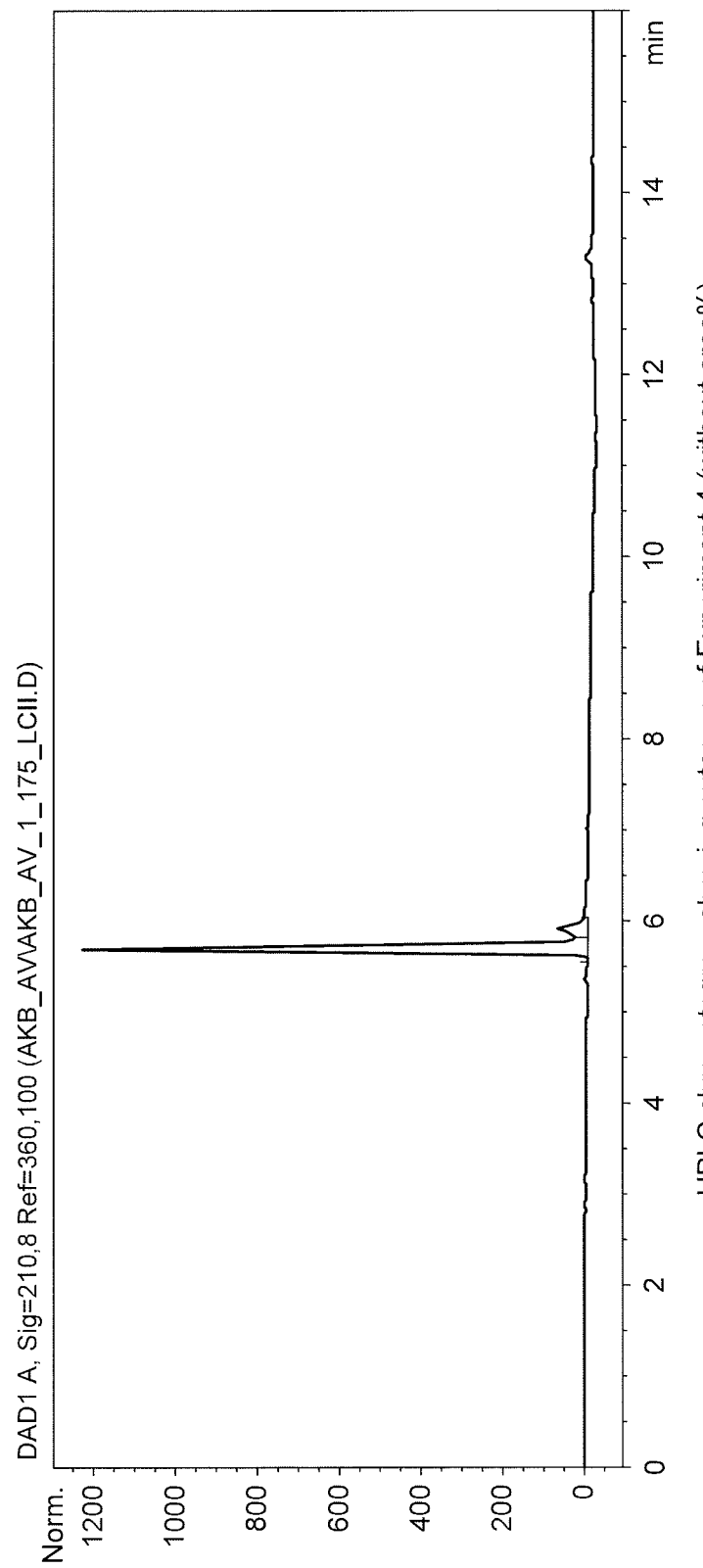
FIG. 5: HPLC chromatogram showing outcome of Experiment 4 (without area %)
Figure 6:
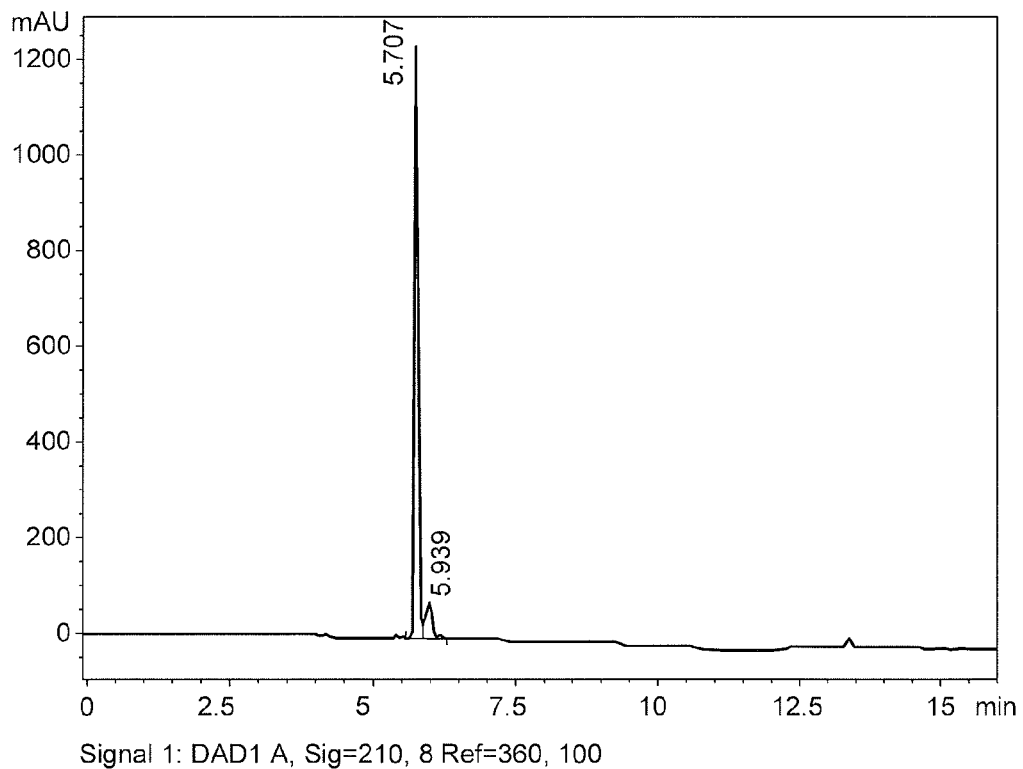
FIG. 6: HPLC chromatogram showing outcome of Experiment 4 (with area %)

FIGS. 3 and 4 show that the impurity from example 2 is not present.

Comparative Example 4

Production of a Polyunsaturated Trifluoroketone Without Anti-Oxidant Produces a Contaminant Migrating Close to the Main Product Peak

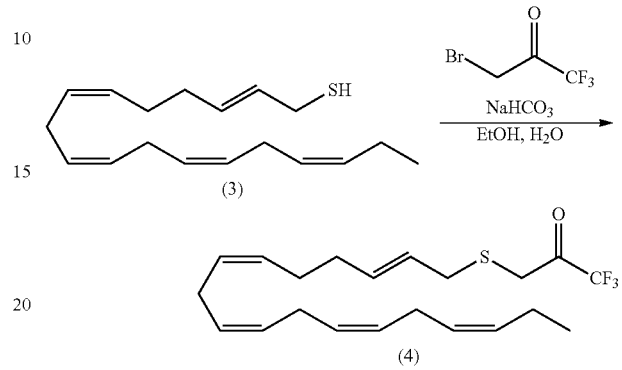

To a solution of (2E,6Z,9Z,12Z,15Z)-octadeca-2,6,9,12,15-pentaene-1-thiol (52.36 g, 189.4 mmol) in ethanol (1200 ml) and water (805 ml) was added sodium hydrogen carbonate (33.48 g, 397.7 mmol) and the reaction mixture stirred at room temperature under nitrogen for 15 minutes. 3-Bromo-1,1,1-trifluoroacetone (23.6 ml, 227.3 mmol) was added in one portion. The reaction mixture was stirred for 40 minutes at room temperature under nitrogen, transferred to a separatory funnel and the aqueous phase extracted with heptane (2×1 l). The organic layer was washed with brine (250 ml), dried (Na$_2$SO$_4$), filtered and concentrated. Dry flash chromatography (heptane : EtOAc gradient) afforded 43.19 g (59%) of 1,1,1-trifluoro-3-(((2E,6Z,9Z,12Z,15Z)-octadeca-2,6,9,12,15-pentaen-1-yl)thio)propan-2-one as a pale yellow oil.

The figures below show chromatograms of the product in the synthesis of AVX001 without presence of anti-oxidant (alpha-tocopherol). The contaminant can be seen in FIGS. 5 and 6 as a shoulder migrating close to the main product peak.

Example 5

Production of a Polyunsaturated Trifluoroketone with Anti-Oxidant Eliminates Presence of the Contaminant

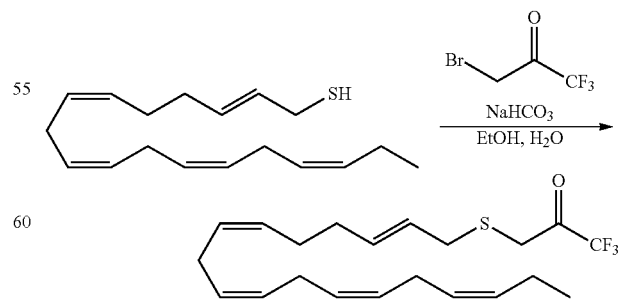

Figure 7:
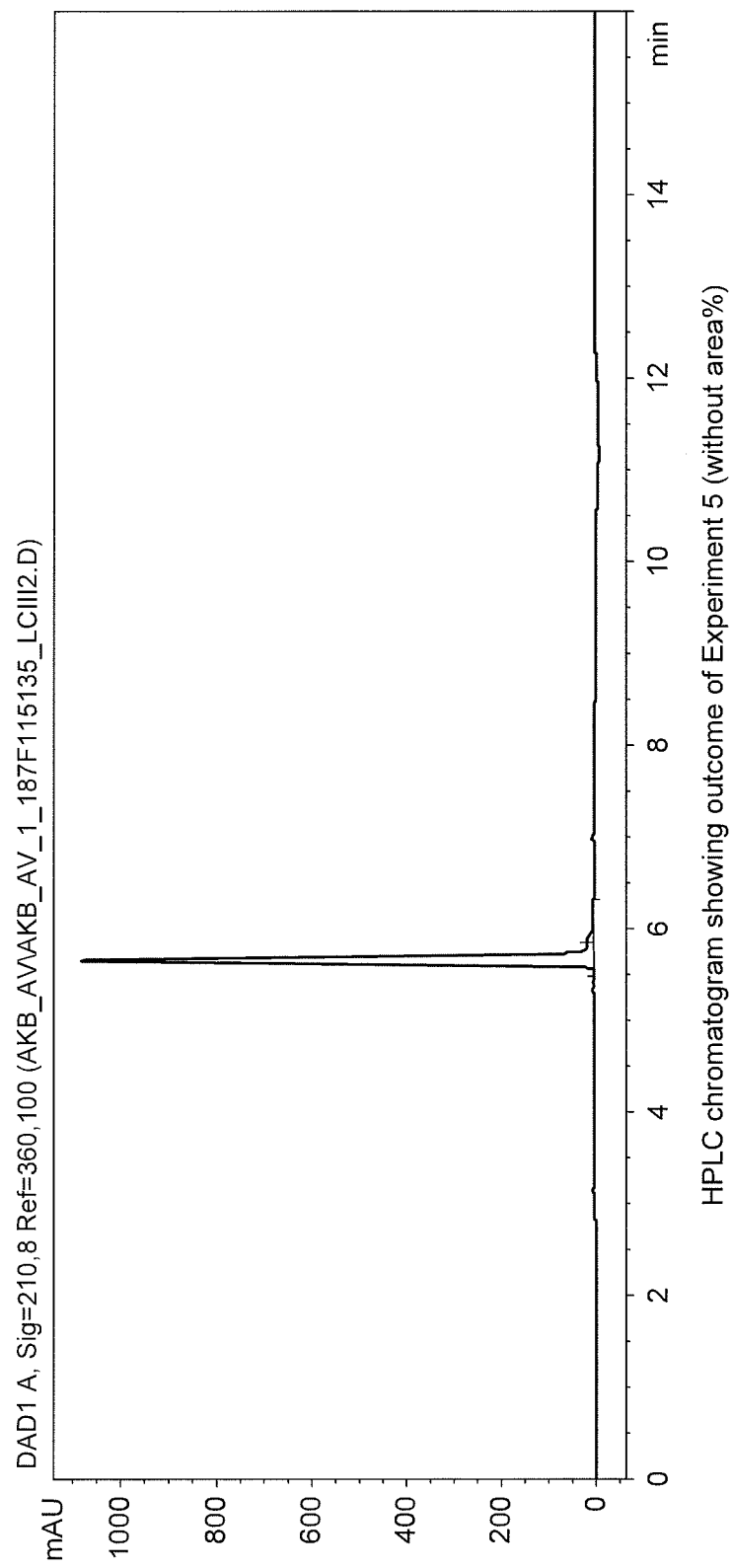
FIG. 7: HPLC chromatogram showing outcome of Experiment 5 (without area %)
Figure 8:
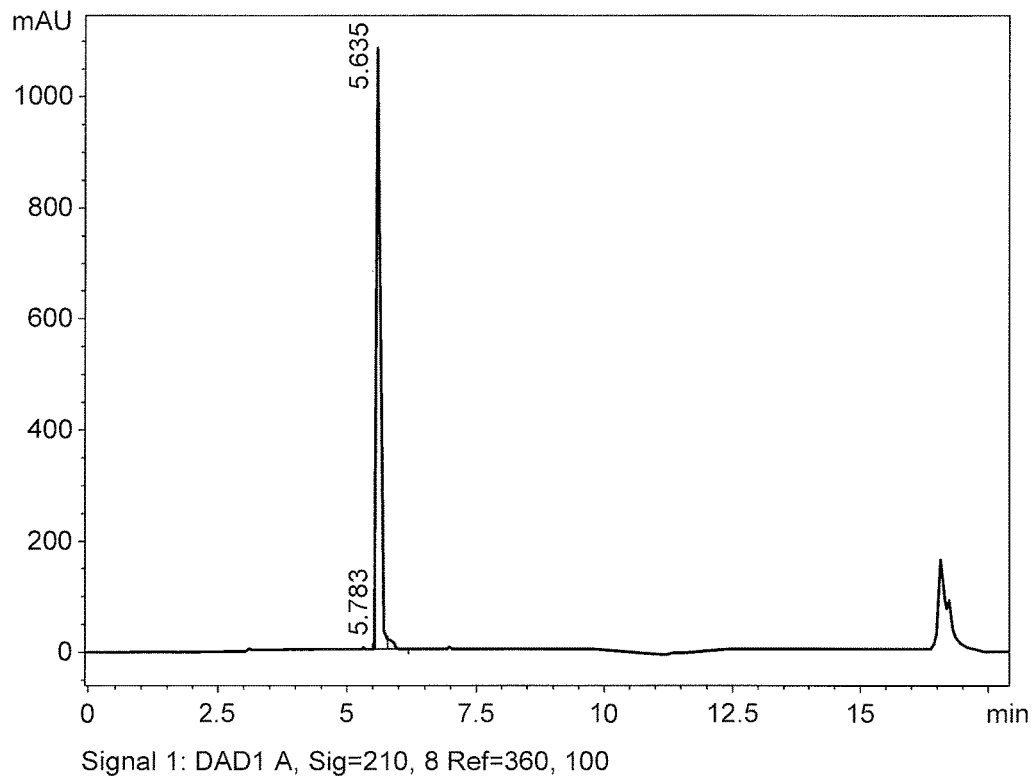
FIG. 8: HPLC chromatogram showing outcome of Experiment 5 (with area %)

To a solution of (2E,6Z,9Z,12Z,15Z)-octadeca-2,6,9,12,15-pentaene-1-thiol (5.06 g, 18.3 mmol) in ethanol (120 ml) and water (80 ml) was added sodium hydrogen carbonate (3.23 g, 38.43 mmol) and the reaction mixture stirred at room temperature under nitrogen for 15 minutes. 3-Bromo-1,1,1-trifluoroacetone (2.3 ml, 22.0 mmol) was added in one portion. The reaction mixture was stirred for 35 minutes at room temperature under nitrogen, transferred to a separatory funnel and the aqueous phase extracted with heptane (2×100 ml). The organic layer was washed with brine (30 ml), dried ($Na_2SO_4$), filtered and concentrated. Flash chromatography (heptane: EtOAc gradient) afforded 5.51 g (78%) of 1,1,1-trifluoro-3-(((2E,6Z,9Z,12Z,15Z)-octadeca-2,6,9,12,15-pentaen-1-yl)thio)propan-2-one as a colorless oil. The FIGS. 7 and 8 show chromatograms of the product in the synthesis of the trifluoroketone with presence of anti-oxidant (alpha-tocopherol). The lights in the fume hoods are to be turned off. No other precautions regarding light protection are considered necessary.

Example 6

Synthesis of 1,1,1-trifluoro-3-(((2E,6Z,9Z,12Z,15Z,)-octadeca-2,6,9,12,15-pentaein-1-yl)thio)propan-2-one (4)

The following shows a procedure for making the polyunsaturated trifluoroketone. To eliminate or reduce presence of unwanted contaminants, thioacid was consumed in a separate reaction before the polyunsaturated alcohol was added. Also, alpha-tocopherol was mixed with the alcohol in a separate reaction chamber to reduce or eliminate unwanted oxidation. These steps and others shown below, were found to increase yields and purity of the compound to 93% or more (area %).

A. Step A (See Scheme I, above)

Triphenylphosphine was weighed (6.05 g±0.10 g), transferred to a 1 liter round bottom flask equipped with a magnetic stirring bar, dissolved in dry THF (310 mL±15 mL), flushed with argon, capped with a septum and immersed in an ice/water bath. The solution was stirred at 0-5° C. for 10-20 minutes. Diisopropyl azodicarboxylate (DIAD) (4.55 mL±0.09 mL) was added the reaction mixture in one portion. The mixture was stirred at 0-5° C. for 30-40 minutes. Thioacetic acid (1.50 mL±0.03 mL) (A) is added the reaction mixture in one portion. The mixture was stirred at 0-5° C. for 15-20 minutes.

Alpha-Tocopherol (10 mg ±0.2 mg) and octadeca-2(E),6(Z),9(Z),12(Z),15(Z)-pentaen-1-ol (C-18 alcohol) (A) were weighed out (5.00 g±0.10 g), was transferred to an Erlenmeyer flask and dissolved in dry THF (50 mL±2.5 mL) and then added to the reaction mixture in one portion. After the addition the cooling bath was removed and the mixture was stirred for 45-55 minutes. The reaction mixture was concentrated under reduced pressure. Temperature in water bath was less than or equal to 30 C. The resulting crude product was analyzed by HPLC (see below). The residue was flushed with argon capped with a septum and placed in the freezer.

The synthesis was performed three times and the batches combined and subjected to purification by chromatography. Purification. Only the crude products that pass the acceptance criterion were combined. To residue, heptane (50 mL±2.5 mL) was added and the flask rotated at the rotavapor for 5-15 minutes at room temperature. The mixture was filtered through a glass sinter funnel (grade 3); Heptane (25 ml±1 mL) was added to the reaction flask, swirled and filtered through the glass sinter funnel. The precipitate was washed with heptane (25 ml±1 mL). The filtrate and washings were concentrated under reduced pressure, temperature in water bath was less than or equal to 30 C. The residue was stored by flushing with argon and capping with a septum and placed in the freezer.

Dry-flash chromatography. Silica gel (500 g±25 g) was transferred to a 1000 mL glass sinter funnel (grade 3) and pre-eluted with heptane 500 mL. Heptane 20-40 mL was added to the crude product and the mixture loaded onto the column. The column was eluted with 250 mL±25 mL fractions. A graded Erlenmeyer flask 250 mL had sufficient accuracy for this purpose. When preparing the heptane: EtOAc (100:1) eluent it was sufficiently accurate to add 25 mL EtOAc to a previously unopened 2500 mL heptane flask. Fractions were analyzed by TLC (eluent heptane:EtOAc 95:5). Product $R_f$ about 0.4, stain with PMA dip or ammonium molybdate/ceric sulfate dip. Elution continued until the entire product was out of the column The fractions were collected where the product was present with a purity of greater than or equal to 93% (area-%) AND the peak at RRT=1.03 was less than or equal to 4% (area-%) and the peak at RRT=0.59 less than or equal to 1% (area-%). Material was transferred to a 1 liter round bottom flask and evaporated under reduced pressure, temperature≤35° C. to obtain 13.5 (73.8%) of the product as a colorless oil. The product was stored at about-18° C. under argon atmosphere.

B. Synthetic Step B—see Scheme I, above

Preparation of solutions. Concentrated HCl (12.3±0.25 mL) was added to a 250 mL graduated cylinder containing some tap water fill with additional tap water to the (150 mL) mark and mix. NaCl (≥40 g) was mixed with tap water (110 mL±10 mL) in an Erlenmeyer flask. The lights in the fume hoods were turned off. No other precautions regarding light protection were considered necessary. alpha-tocopherol (27.2 mg) was weighed out and MeOH (130 ml) was weighed out, and dissolved and transferred to the 1 liter round bottom flask with thioacetic acid S-octadeca-2(E),6(Z),9(Z),12(Z),15(Z)-pentaenyl ester (13.5 g) equipped with a magnetic stirring bar and a 100 ml dropping funnel. $K_2CO_3$ (6.45 g) was added to the reaction mixture in one portion. Flush with argon and cap with a septum. Stir at room temperature for 30-40 minutes. The reaction flask was immersed in an ice/water bath and 1M HCl (150 mL) was added carefully drop wise through the dropping funnel, then transferred to a separatory funnel and extracted with heptanes [2×200 mL]. The combined organic phase was washed with brine (100 mL), transferred to an Erlenmeyer flask equipped with a magnetic stirring bar and $Na_2SO_4$ (70.4 g) was added. If required, additional $Na_2SO_4$ can be added. The suspension was stirred for 10-20 minutes. The suspension was filtered, and the filter cake rinsed with heptane (≥25 mL), transferred to a 1 L round bottom flask and evaporated under reduced pressure, temperature≤35° C. This crude product (12.0 g, quantitative yield) was used in the next step without further purification. The product was stored at less than or equal to −18° C. under argon atmosphere.

C. Preparation of Polyunsaturated Trifluoroketone (see Scheme I)

Preparation of Solutions

NaCl (≥40 g) was mixed with tap water (I) (110 mL). The lights in the fume hoods were turned off. No other precautions regarding light protection were considered necessary. $NaHCO_3$ (7.68 g) was weighed out and EtOH (290 mL) and tap water (192 mL) was measured and transferred to the 1 liter flask containing octadeca-2(E),6(Z),9(Z),12(Z),15(Z)-pentaene-1-thiol (12.0 g) and flush with argon. It was stirred vigorously at room temperature for 15-20 minutes. 3-bromo-1,1,1-trifluoroacetone (5.4 mL) was added in one portion and stirred vigorously for 35-45 minutes. Material was transferred to a separatory funnel and extracted with heptane (I) (2×200 mL). Combined organic phase was washed with brine (100 mL), and transferred to an Erlenmeyer flask equipped with a magnetic stirring bar and added $Na_2SO_4$ (I) (60 g). If required additional $Na_2SO_4$ can be added. The suspension was stirred for at 10-20 minutes.

The suspension was filtered, and the filter cake rinsed out with heptane (≥25 mL), and transferred to a 1 L round bottom flask and evaporated under reduced pressure, temperature (≤35° C.).

Dry-flash chromatography. Silica (500 g±25 g) was transferred to a 1000 mL glass sinter funnel (grade 3). Pre-eluted with heptane 500±25 mL. Heptane 20-25 mL was added to the crude product and the mixture loaded onto the column. The column was eluted with 350 mL±20 mL fractions. A graded 500 mL Erlenmeyer flask has sufficient accuracy for this measurement. When preparing the heptane:EtOAc (100:x) eluent it was sufficiently accurate to add 25× mL EtOAc to a previously unopened 2500 mL heptane flask. The fractions were analyzed by TLC (eluent heptane:EtOAc 80:20). Product $R_f$ of about 0.26, stain with PMA dip or ammonium molybdate/ceric sulfate dip. Continue elution until the entire product is out of the column. Elute with heptane—heptane:EtOAc (100:1)-(100:2)-(100:3)-(100:10). If the impurities in front of the product are out of the column after fraction #21, (100:10) can be used from fraction #22, otherwise continue with (100:2) or (100:3). When the impurities in front of the product are out of the column (100:10) can be used.

Analyze by HPLC the fractions that by TLC are pure or with only small amounts of impurities. Collect the fractions containing product with purity within HPLC specs (area-%). Material was transferred to a 1 liter round bottom flask and evaporated under reduced pressure, temperature≤35° C. A rotavapor was filled with argon when pressure was equilibrated. Heptane was used to transfer to a 250 mL round bottom flask through a folding filter and evaporate under reduced pressure, temperature (≤35° C.). When the initial evaporation was finished, a high vacuum pump was connected to the rotavapor and evaporate for 1-2 hrs to obtain 10.29 g (61%) of the product as a colorless oil. The product was stored at less than or equal to −18° C. under argon atmosphere.

The following materials and methods were used as needed in this Example 6.

1. TLC: A small sample of product was analyzed as needed by TLC with heptane:EtOAc (80:20) as eluent. Product $R_f$ approx 0.26, stain with PMA dip or ammonium molybdate/ceric sulfate dip. Only small amounts of impurities are tolerated.

2—HPLC

HPLC/UV Conditions

Analytical column: EC-C18, 150×4.6 mm, 2.7 μm particle size

Flow: 1.5 ml/min

Stop time: 22 min

Temperature: 15° C.

Detector: UV 210:8 ref 360:100 PW>0.05 min

Mobile phases: A: ACN/Water 70:30 w/0.02% v/v formic acid

B: ACN w/0.02% v/v formic acid

|  | Time | % B |
|---|---|---|
| Mobile phase gradient program: | Initial | 0% |
|  | 12 min | 80% |
|  | 20 min | 100% |

The invention claimed is:

1. A process comprising:
   (1) combining, in a first vessel, a carboxylic acid or thioacid in the presence of a phosphine and an azodicarboxylate compound under conditions that deprotonate essentially all of the carboxylic acid or thioacid therein;
   (2) combining, in a second vessel, a polyunsaturated alcohol and at least one pharmaceutically acceptable anti-oxidant; and
   (3) mixing the contents of the first and second vessels so as to form a said polyunsaturated ester or thioester.

2. A process for the preparation of a polyunsaturated thiol comprising:
   (1) combining, in a first vessel, a thioacid in the presence of a phosphine and an azodicarboxylate compound under conditions that deprotonate essentially all of the thioacid therein;
   (2) combining, in a second vessel, a polyunsaturated alcohol and at least one pharmaceutically acceptable anti-oxidant;
   (3) mixing the contents of the first and second vessels so as to form a polyunsaturated thioester; and
   (4) adding at least one pharmaceutically-acceptable anti-oxidant to the polyunsaturated thioester of step (3), which may be the same or different from the anti-oxidant used in step (2), and reducing the thioester from step (3) under conditions sufficient to make the polyunsaturated thiol.

3. A process for the preparation of a polyunsaturated ketone compound comprising:
   (1) combining, in a first vessel, a thioacid in the presence of a phosphine and an azodicarboxylate compound under conditions that deprotonate essentially all of the thioacid therein;
   (2) combining, in a second vessel, a polyunsaturated alcohol of formula ROH where R is a C9-23-polyunsaturated hydrocarbon and at least one pharmaceutically acceptable anti-oxidant;
   (3) mixing the contents of the first and second vessels so as to form a polyunsaturated thioester;
   (4) adding at least one pharmaceutically-acceptable anti-oxidant to the polyunsaturated thioester of step (3), which may be the same or different from the anti-oxidant used in step (2), and reducing the thioester from step (3) under conditions sufficient to make a polyunsaturated thiol, RSH; and
   (5) reacting said polyunsaturated thiol with a compound (LG)R³COX wherein X is an electron withdrawing group and R³ is a $C_{1-3}$ alkylene group carrying a leaving group LG, optionally in the presence of further added antioxidant, so as to form the polyunsaturated ketone compound of formula (II)

$$R^2-CO-X \tag{II}$$

wherein $R^2$ is a C10-24 polyunsaturated hydrocarbon group interrupted (β, γ, or δ position from the ketone group by a S atom; and X is an electron withdrawing group.

4. The process of claim 1, wherein the pharmaceutically acceptable anti-oxidant is tocopherol.

5. The process of claim 1, wherein the polyunsaturated thioester is at least 90% pure as determined by HPLC (% area).

6. The process of claim 5, wherein the polyunsaturated thioester is at least 91%, 92%, 93%, 94% or at least 95% pure as determined by HPLC (% area).

7. The process of claim 3, wherein the polyunsaturated ketone is at least 90% pure as determined by HPLC (% area).

8. The process of claim 7, wherein the polyunsaturated ketone is at least 91%, 92%, 93%, 94% or at least 95% pure as determined by HPLC (% area).

9. The process of claim 1, wherein the phosphine is triphenylphosphine.

10. The process of claim 1, wherein the azodicarboxylate is diisopropyl azodicarboxylate (DIAD).

11. The process of claim 1 wherein there is a molar excess of phosphine and azodicarboxylate to thioacid or acid in step (1).

12. The process of claim 1, wherein the polyunsaturated alcohol is of formula (I)

wherein R is an optionally substituted $C_{9-23}$ unsaturated hydrocarbon group optionally interrupted by one or more heteroatoms or groups of heteroatoms selected from S, O, N, SO, $SO_2$, said hydrocarbon group comprising at least 2, preferably at least 4 double bonds.

13. The process of claim 1, wherein the polyunsaturated alcohol is a C18 alcohol comprising 5 double bonds.

14. The process of claim 13 wherein the polyunsaturated alcohol is (2E, 6Z, 9Z, 12Z, 15Z)-octadeca-2,6,9,12,15-pentaen-1-ol.

15. The process of claim 1, wherein the polyunsaturated thioester is a C18 polyunsaturated thioacetic acid ester comprising 5 double bonds.

16. The process of claim 15, wherein the polyunsaturated thioacetic acid ester is S-((2E, 6Z, 9Z, 12Z, 15Z,)-octadeca-2,6,9,12,15-pentaein-1-yl) ethanethioate.

17. A process as claimed in claim 1 comprising the steps:
A) combining, in a first vessel, a phosphine, an azodicarboxylate and thioacetic acid in solvent to form a mixture and allowing complete deprotonation of said thioacetic acid to occur;
B) combining, in a second vessel, (2E, 6Z, 9Z, 12Z, 15Z)-octadeca-2,6,9,12,15-pentaen-1-ol (C18 allylic alcohol) and an anti-oxidant;
C) mixing the contents of the first and second vessels to make S-((2E, 6Z, 9Z, 12Z, 15Z,)-octadeca-2,6,9,12,15-pentaein-1-yl) ethanethioate.

18. A process as claimed in claim 17 further comprising:
D) optionally subjecting the ester produced in Step C) to dry-flash chromatography under conditions that purify the ester to at least 90% purity as determined by HPLC (% area);
E) contacting the optionally purified S-((2E, 6Z, 9Z, 12Z, 15Z,)-octadeca-2,6,9,12,15-pentaein-1-yl) ethanethioate produced in Step C) or D) with a metal carbonate and tocopherol under conditions that reduce the ester group and produce the corresponding thiol (2E, 6Z, 9Z, 12Z, 15Z)-octadeca-2,6,912,15-pentaene-1-thiol).

19. A process as claimed in claim 18 further comprising:
F) contacting the thiol produced in step E) with 3-bromo-1,1,1-trifluoroacetone under conditions that produce:

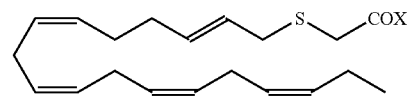

where X is $CF_3$.

20. A process as claimed in claim 3, wherein the ketone is

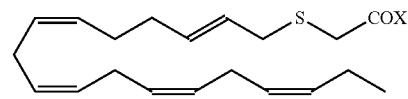

where X is $CF_3$.

21. A process as claimed in claim 1 wherein the polyunsaturated alcohol is obtained by reduction of its corresponding aldehyde in the presence of an electrophilic reducing agent such as DIBAH.

22. A process as claimed in claim 1 wherein in step 2) the polyunsaturated alcohol is (3Z, 6Z, 9Z, 12Z, 15Z)-octadeca-3,6,9,12,15-pentaen-1-ol and the mixing step (3) makes an S-((3Z, 6Z, 9Z, 12Z, 15Z,)-octadeca-3,6,9,12,15-pentaen-1-yl) thioester.

23. A process as claimed in claim 1 comprising the steps:
1) combining, in a first vessel, a phosphine, an azodicarboxylate and thioacetic acid in solvent to form a mixture and allowing complete deprotonation of said thioacetic acid to occur;
2) combining, in a second vessel, (3Z, 6Z, 9Z, 12Z, 15Z)-octadeca-3,6,9,12,15-pentaen-1-ol (C18 allylic alcohol) and an anti-oxidant;
3) mixing the contents of the first and second vessels to make S-((3Z, 6Z, 9Z, 12Z, 15Z,)-octadeca-3,6,9,12,15-pentaen-1-yl) ethanethioate.

24. A process as claimed in claim 22 comprising adding at least one pharmaceutically-acceptable anti-oxidant to the S-((3Z, 6Z, 9Z, 12Z, 15Z,)-octadeca-3,6,9,12,15-pentaen-1-yl) thioester of step (3), which may be the same or different from the anti-oxidant used in step (2), and reducing the thioester from step (3) under conditions sufficient to make (3Z, 6Z, 9Z, 12Z, 15Z)-octadeca-3,6,912,15-pentaen-1-thiol).

25. A process as claimed in claim 23 comprising, optionally:
4) subjecting the ethanethioate produced in Step 3) to dry-flash chromatography under conditions that purify the ester to at least 90% purity as determined by HPLC (% area); and
5) contacting the optionally purified S-((3Z, 6Z, 9Z, 12Z, 15Z,)-octadeca-3,6,9,12,15-pentaen-1-yl) ethanethioate produced in Step 3) or 4) with a metal carbonate, such as potassium carbonate, and tocopherol under conditions that reduce the ester group and produce the corresponding thiol (3Z, 6Z, 9Z, 12Z, 15Z)-octadeca-3,6,912,15-pentaen-1-thiol).

26. A process as claimed in claim 24 comprising:
contacting the thiol with 3-bromo-1,1,1-trifluoroacetone under conditions that produce the polyunsaturated ketone:

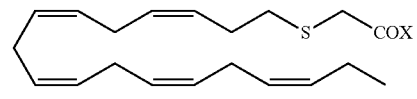

where X is $CF_3$.

27. A process as claimed in claim 25 comprising:
contacting the thiol with 3-bromo-1,1,1-trifluoroacetone under conditions that produce the polyunsaturated ketone:
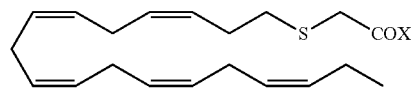
where X is $CF_3$.

UNITED STATES PATENT AND TRADEMARK OFFICE
CERTIFICATE OF CORRECTION

Page 1 of 1

PATENT NO.        : 10,093,618 B2
APPLICATION NO.   : 14/907147
DATED             : October 9, 2018
INVENTOR(S)       : Marcel Sandberg et al.

It is certified that error appears in the above-identified patent and that said Letters Patent is hereby corrected as shown below:

On the Title Page

Item (12) "Sanderberg et al." should read -- Sandberg et al. --.

Item (72) Delete "Sanderberg" and insert -- Sandberg --.

Signed and Sealed this
Twenty-fourth Day of September, 2019

Andrei Iancu
*Director of the United States Patent and Trademark Office*